United States Patent [19]

Koizumi et al.

[11] Patent Number: 4,954,319

[45] Date of Patent: Sep. 4, 1990

[54] MECHANISM FOR SUPPLYING ANALYTICAL TAPE FOR BIOCHEMICAL ANALYSIS BY PREDETERMINED LENGTH

[75] Inventors: Takashi Koizumi; Hideo Ishizaka, both of Kanagawa, Japan

[73] Assignee: Fuji Photo Film Co., Ltd., Kanagawa, Japan

[21] Appl. No.: 284,638

[22] Filed: Dec. 15, 1988

[30] Foreign Application Priority Data

Dec. 16, 1987 [JP] Japan .............................. 62-318149
Dec. 16, 1987 [JP] Japan .............................. 62-318150

[51] Int. Cl.$^5$ ........................................... G01N 35/00
[52] U.S. Cl. ......................................... 422/67; 422/66; 436/44
[58] Field of Search ................. 436/44; 422/66, 67; 377/18; 242/186, 199, 200

[56] References Cited

U.S. PATENT DOCUMENTS

| | | | |
|---|---|---|---|
| 3,526,480 | 9/1970 | Findl et al. | 422/66 |
| 3,825,410 | 7/1974 | Bagshawe | 422/66 |
| 3,849,661 | 11/1974 | Beiter | 377/18 |
| 3,979,181 | 9/1976 | Plakas | 422/66 |
| 4,044,233 | 8/1977 | Sato | 360/137 |
| 4,163,532 | 8/1979 | Sakai | 242/186 |
| 4,568,520 | 2/1986 | Ackermann et al. | 436/44 |
| 4,696,439 | 9/1987 | Sukigara et al. | 242/186 |

Primary Examiner—Robert J. Warden
Assistant Examiner—D. John Griffith, Jr.
Attorney, Agent, or Firm—Sughrue, Mion, Zinn, Macpeak & Seas

[57] ABSTRACT

A new mechanism for supplying in sequence unused regions of an analytical tape by predetermined length to an analytical section arranged in an apparatus for biochemical analysis of a liquid sample is disclosed. The mechanism comprises a driving means for moving the analytical tape to supply its unused regions to the analytical section; a means for detecting length of the unused regions of the tape supplied to the analytical section comprising a roller which is arranged in contact with a surface of the tape so that it rotates with movement of the tape for the supply of the unused regions to the analytical section and a means for detecting number or angle of the rotation of the roller, and a means for controlling operation of the driving means according to the detected number or angle of the rotation of the roller.

9 Claims, 6 Drawing Sheets

MECHANISM FOR SUPPLYING ANALYTICAL TAPE FOR BIOCHEMICAL ANALYSIS BY PREDETERMINED LENGTH

BACKGROUND OF THE INVENTION

This invention relates to a mechanism for supplying in sequence unused regions of an analytical tape by predetermined length to an analytical section of an apparatus for biochemical analysis of a liquid sample. At the analytical section of the apparatus, the liquid sample is supplied onto the analytical tape, the applied sample is incubated, and the incubated sample is then subjected to photometric measurement for the desired analysis.

It is important for clinical chemical examination in the present medical treatment to quantitatively determine amounts of various analytes in body fluids (whole blood, plasma, serum, urine, saliva, etc.) so as to make accurate diagnosis and proper treatment. Moreover, a number of such clinical chemical examinations should be made rapidly. Accordingly, there are requirements in medical institutions and laboratories to provide methods and apparatus for carrying out the above quantitative analysis simply, automatically and continuously.

For the purpose of performing such quantitative analysis, biochemical analytical methods using a multilayer analytical element utilizing spectrophotometric measurement and an analytical element for measuring ion activity by the use of ion-selective electrodes have been proposed and put to practical use.

In the analysis using the multilayer analytical element (hereinafter sometimes referred to as colorimetric analytical element), a small amount of a liquid sample to be analyzed is applied (spotted) on the colorimetric analytical element and incubated at a given temperature for a given period of time to produce a color reaction between an analyte in the liquid and a reagent in the element, and then the analyte is quantitatively determined by measuring color density by spectrophotometry.

In the analysis using the analytical element by utilizing ion-selective electrodes, a liquid sample to be analyzed and a reference solution are applied onto each of ion-selective layers electrically separated from each other in the ion-selective electrodes and electrically connected to each other through a bridge, and a potential difference between the ion-selective electrodes is measured to determine the ion activity of the liquid sample.

To conduct automatically and continuously and analysis by using the analytical elements for biochemical analysis, it is convenient to use a long film (i.e., analytical tape) as disclosed in U.S. Pat. No. 3,526,480. It may be considered that the analytical tape (continuous tape) for biochemical analysis is wound up to form a roll, placed in a cassette and placed in a biochemical analyzer, and that a portion of the analytical tape having been used for analysis is wound up into a roll and placed in a cassette.

In performing the analysis, the analytical tape ought to be intermittently supplied to the analysis section of an analyzer by a given length. As the supply method, it can be considered that a roll shaft of the cassette for winding up the used portion of the analytical tape is intermittently rotated by a given number of rotations of the shaft or an angle of the shaft to move the analytical tape intermittently. In this method, however, the winding diameter of the roll for winding up the analytical tape is gradually changed with an increase of the amount of the wound-up film portion and the thickness of the film varies depending on the type of the tape. Accordingly, it is difficult to supply intermittently the analytical tape by a given length throughout a series of the analytical operations.

SUMMARY OF THE INVENTION

An object of the present invention is to provide a mechanism which can easily and accurately supply unused regions of an analytical tape to an analytical section by a predetermined length for use in biochemical analysis.

The present invention provides a mechanism for supplying (i.e., feeding) in sequence unused regions of an analytical tape by a predetermined length to an analytical section arranged in an apparatus for biochemical analysis of a liquid sample. At the analytical section, the liquid sample is applied onto the unused region of the analytical tape, of the applied sample is incubated, and photometric measurement of the incubated sample is performed. One end and the unused regions following said end of the analytical tape are encased in a cassette and another end of the analytical tape is encased in another cassete for receiving the used regions of the analytical tape after the photometric measurement is completed. The mechanism comprises:

a driving means for moving the analytical tape to supply its unused regions to the analytical section;

a means for detecting length of the unused regions of the tape supplied to the analytical section comprising a roller which is arranged in contact with a surface of the analytical tape so that it rotates with movement of the analytical tape for the supply of the unused regions to the analytical section and a means for detecting number or angle of the rotation of the roller; and a means for controlling operation of the driving means according to the detected number or angle of the rotation of the roller.

In one embodiment (A) of the invention, the detecting means comprises a roller which is provided between the analytical section and either the cassette for the unused tape regions or the cassette for the used tape regions.

In another embodiment (B) of the invention, the detecting means comprises a roller which is arranged within either one of the cassettes in the vicinity of the inlet and outlet of an analytical tape. The roller may have a detectable mark provided at an eccentric position on its side face (i.e., circular flat side face). Alternatively, the roller is equipped with a rotor having a detecting mark at an eccentric position on its side face. The rotor rotates synchronously with said roller.

BRIEF DESCRIPTION OF THE DRAWINGS

FIG. 3b is a cross-sectional view taken along the line B—B in FIG. 3a.

DETAILED DESCRIPTION OF THE INVENTION

The embodiment (A) of the tape supplying mechanism of the present invention will be illustrated in detail below.

Figure 1:
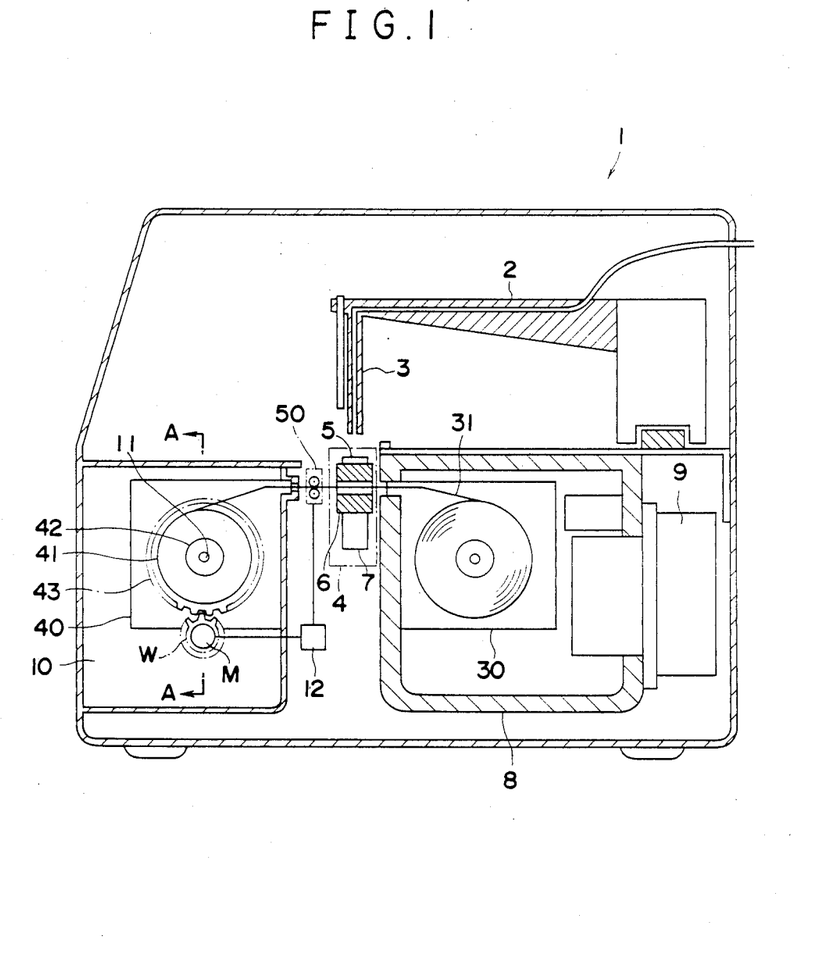
FIG. 1 is a schematic cross-sectional view of an embodiment of a biochemical analytical apparatus for use in colorimetric analysis, which is provided with a mechanism of the embodiment (A) according to the invention for supplying in sequence unused regions of an analytical tape by a predetermined length.
Figure 2:
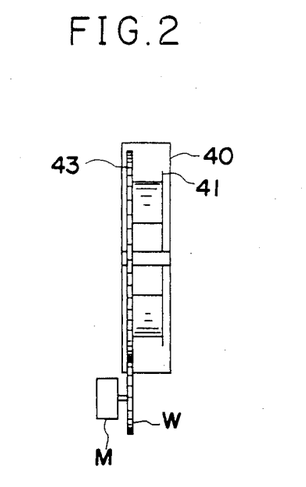
FIG. 2 is a cross-sectional view of a part of the cassette taken along the line A—A in FIG. 1.

Referring to FIGS. 1 and 2, at the upper part of the biochemical analytical apparatus 1 there is provided a means 2 for spotting a liquid sample containing analyte. A spotting nozzle 3 connected to the spotting means 2 is provided just above an analytical section 4 which is arranged in the vicinity of center of the analytical apparatus 1. The spotting means 2 is provided movably on the plane vertical to the direction of movement of the analytical tape. The analytical section 4 is provided with a shutter 5, an incubator 6 and a photometric measuring device 7. If desired, a plurality of the analytical sections may be placed on the line vertical to the direction of the movement of the analytical tape. Further, the analytical section 4 may be provided on the line in such a manner that the section can be moved in association with the spotting means 2. In the lower half part of the biochemical analytical apparatus 1, there is provided a low-temperature insulation container 8 having a cassette 30 for the unused portion of the analytical tape which is charged with an analytical tape 31. The insulation container 8 can be adjusted to have a desired low temperature and low humidity by a dehumidifying cooler 9 and can be kept at the adjusted low temperature and humidity. On the side opposed to the low-temperature insulation container 8, there is provided a wind-up chamber 10 which contains a cassette 40 for receiving the used portion of the analytical tape in such a way that the analytical section 4 is placed between the two cassettes. In the wind-up chamber 10, there is provided a motor M which has a gear W meshing with teeth on the outer periphery of a spool wheel 43 fixed to a reel 41 for winding up the used tape portion and causes rotation of the reel 41.

A means 50 for detecting the feed length (length supplied by action of driving means) of an analytical tape is positioned between the analytical section 4 and the wind-up chamber 10. Between the detecting means 50 and the motor M, there is provided a control means 12 for controlling the action (start and stop) of the motor M according to signals delivered from the detecting means 50.

In making the analysis of a liquid sample by using the biochemical analytical apparatus 1, the analytical tape 31 drawn out of the cassette 30 is moved to the analytical section 4; a liquid sample is spotted (deposited) through the spotting nozzle 3 on the analytical tape 31; the incubator 6 is closed by means of the shutter 5; the temperature of the incubator is adjusted to, for example, 37° C. and incubation is carried out for a certain period of time. During or after the incubation, the optical density of the analytical tape 31 at the sample spotted area is measured by the photometric measuring device 7.

After a series of the analytical operations from the spotting of the liquid sample to the measurement of the optical density is made in the analytical section 4, the analytical tape is wound up around a reel in the cassette for used portion by actuating the motor M, and another unused portion of the analytical tape 31 is moved to the analytical section 4. This operation must be conducted in such a manner that any piece of the portion of the analytical tape used for the previous analysis is not left behind in the analytical section 4 and the analytical tape 31 must always be moved by a given length required for the analysis so that any unused portion of tape 31 is not wasted by moving an extra length of the unused tape portion.

Figure 3A:
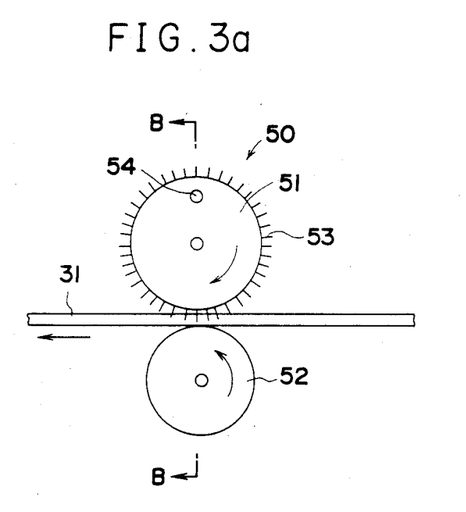
FIG. 3a is an enlarged cross-sectional view of the embodiment (A) of means for detecting the feed length (length supplied by an action of driving means) of an analytical tape.

In FIG. 3a, the analytical tape 31 is moved in the direction of the illustrated arrow, by rotation of the motor M which drives the spool wheel 43 in the cassette 40 (see FIG. 1), and the tape 31 is wound up by the reel 41. The analytical tape 31 is held between rollers 51 and 52 so that it is not slipped on the front and back surfaces. A great number of needle-like protrusions 53 are provided on the periphery of the roller 51. Since the upper surface of the analytical tape 31 is composed of generally paper, knitted fabric, woven fabric, non-woven fabric or the like as described below, the needle-like protrusions 53 are locked with the upper surface of the analytical tape so that the roller 51 follows the movement of the analytical tape 31 and is accurately rotated in association with the movement of the tape without causing slippage of the roller 51 and the analytical tape 31. The locking of the needle-like protrusions 53 with the analytical tape 31 can be easily made. Therefore, force required for pressing the analytical tape 31 by the rollers 51, 52 is small and the force required for the roller 52 is merely at a level to support the analytical tape 31. The roller 51 is provided with a through-hole 54 at an eccentric position on its flat side surface. The hole 54 can be detected by a combination of a light-emitting device 55 such as a light-emitting diode provided on one side of the roller 51 and a light receiving device 56 such as a photodiode provided on the other side thereof.

Figure 3B:
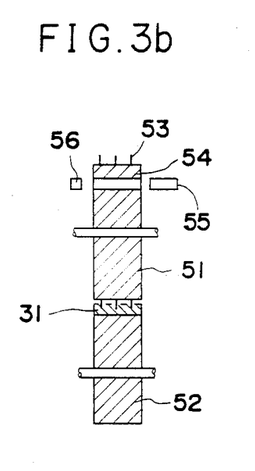

The means for detecting the feed length of the analytical tape is constructed as shown in FIGS. 3a and 3b. Accordingly, in the movement of the analytical tape 31, the number of times of the passage of the hole 54 on a line joining the light emitting device 55 and the light receiving device 56 to each other by the rotation of the roller 51 which rotates following the movement of the analytical tape 31 is detected. At the time when a predetermined length of the analytical tape is moved, a signal is fed to the control means 12 and the rotation of the motor M is stopped by the instructions from the control means 12 to thereby stop the rotation of the reel 41, thus stopping the movement of the analytical tape 31. At this moment, the unused tape region is positioned in the analytical section 4 to carry out analysis of a liquid sample. When the analysis is complete, another signal is fed to the control means 12, and the motor M is started by the instructions from the control means 12 to rotate the reel 41 to thereby move the analytical tape. Then, the feed length is detected in the same manner as above. At the time when a predetermined length of the analytical tape is fed, the movement of the analytical tape 31 is stopped. By repeating the operations described above, unused regions of the analytical tape 31 can be intermittently supplied to the analytical section by just a given length required for the analysis.

The feed length of the analytical tape 31 can be arbitrarily changed by properly choosing the diameter of the roller 51, the number of rotation (revolution) of the roller, etc.

The analytical tape of a length required for one analytical operation may be supplied by one to several revolutions of the roller 51. Alternatively, the roller 51 may be provided with a plurality of holes (detectable marks) at regular intervals and the analytical tape of a length required for one analytical operation may be moved by less than one revolution (e.g., ½ revolution, ⅓ revolution, a certain angle, or the like).

Many acute-angled protrusions may be provided on the surface of the roller 51 by forming a ratchet or rasp or by partially embedding solid particles on the surface of the roller 51, instead of providing the needle-like protrusions 53.

The lower roller 52 may be replaced with a flat guide plate supporting the analytical tape 31.

Only side edge parts of the analytical tape 31 may be held between two rollers having a smooth periphery by pressing, where width of the analytical tape is large.

The light emitting device 55 and the light receiving device 56 for detecting the hole 54 may be arranged in reverse order to that described above. Further, an appropriate detectable mark (e.g., color mark, magnetic layer, protrusion, etc.) may be provided at the same position as that of the hole 54 in place of the hole 54 and the number or angle of rotation of the roller 51 may be detected by detecting said mark optically (reflected light), electromagnetically or mechanically.

The means for detecting the feed length of the analytical tape may be provided between the low-temperature insulation container 8 and the analytical section 4.

Where the detecting means is arranged between the analytical section 4 and the wind-up chamber 10, there may be a problem that the roller 51 is stained with a liquid sample spotted on the analytical tape 31, while a risk of damaging the analytical tape 31 by the contact of the analytical tape 31 with the rollers 51, 52 can be avoided. Where the detecting means is arranged between the analytical section 4 and the low-temperature insulation chamber 8, there may be a problem that the analytical tape 31 would be damaged by the contact of the analytical tape 31 with the rollers 51, 52, while the roller 51 is assured to be kept clean. The position where the detecting means is to be arranged can be properly determined by taking the types of the analytical apparatus, and the analytical tape, analytical methods, etc. into consideration.

While an embodiment wherein the reel 41 is rotated by the spool wheel 43 driven by the motor M is illustrated in FIG. 1, the wind-up shaft 11 may be locked with the hole 42 of the reel 41, or the wind-up shaft 11 may be directly or indirectly rotated by the motor M without providing the spool wheel 43.

Figure 4:
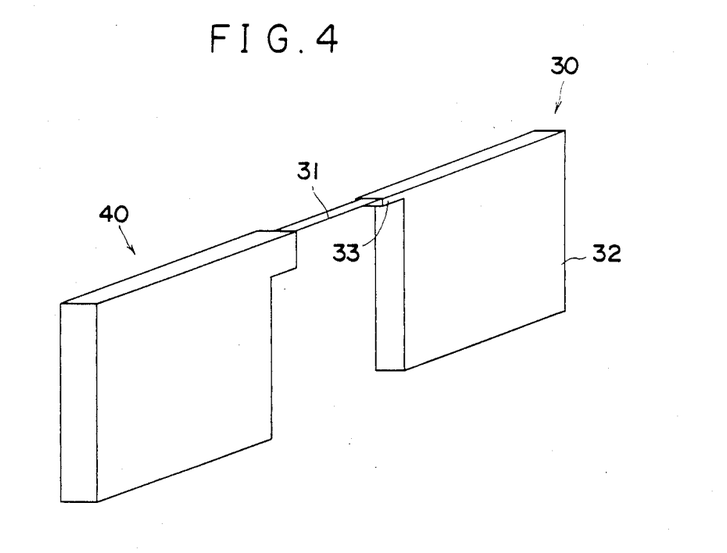
FIG. 4 is a perspective view showing one embodiment of an analytical tape cassette for use in biochemical analysis.

In FIG. 4, the cassette 30 for unused tape portion is a thick-wall rectangular case which has side plates 32 having a form of nearly a square, is slightly wider than the width of the analytical tape 31 and contains a roll of the analytical tape 31 therein. A port 33 for drawing out the analytical tape 31 is projecting from the case body. Another cassette 40 for used tape portion is a case having similar form and size to those of the cassette for unused tape portion 30 and has such a structure that the used tape portion is wound up around a reel or the like in the case.

The above-described cassette cases can be prepared by any of conventional methods. For example, the box and lid of the cassette case are separately prepared and the unused tape is charged into the box. Thereafter, the box is fixed to the lid by means of fitting, locking, screwing, adhesion or the like. Alternatively, the box and the lid may be integrally prepared by joining them with each other by one side of them to form the joint in the form of a hinge structure.

The diameter of a reel (not shown) for winding the analytical tape 31 into a roll in the cassette 30 should be not very small, because there is a fear that the analytical tape 31 is cracked when the analytical tape 31 is wound at a too small curvature radius. Generally, the diameter of the reel preferably is in the range of 40 to 80 mm. If desired, an appropriate locking member may be provided inside the reel to prevent the analytical tape from being excessively drawn out.

The cassette case and the reel can be easily prepared from various thermoplastic resins such as polyolefin resins (e.g., polyethylene and polypropylene), styrene resins (e.g., polystyrene, impact-resistant polystyrene, styrene-acrylonitrile resin, and ABS resin), vinyl chloride resins, polyamides, polyesters, polycarbonates, polyacetal and other resins by any of techniques which are used for production of audio and video cassette tapes.

If desired, the cassette 30 for unused tape portion may be prepared integrally with the cassette 40 for used tape portion.

Figure 5:
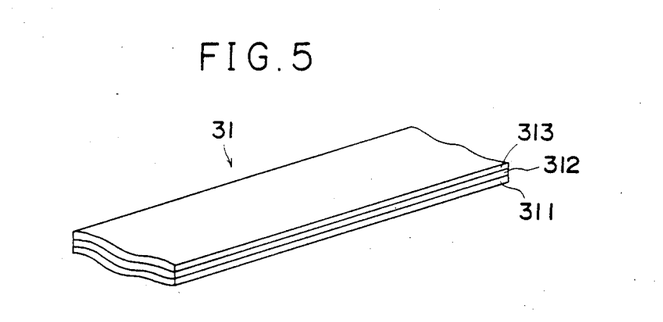
FIG. 5 is a perspective view of one embodiment of an analytical tape for use in colorimetry.

An example of the analytical tape 31 is one for use in colorimetry. A tape in the form of a multilayer analytical element as shown in FIG. 5. In FIG. 5, the analytical tape 31 for colorimetry comprises a spreading layer 313, a reagent layer 312 and a light-transmissive support 311 wherein the reagent layer 312 is laminated onto the support 311 and the spreading layer 313 is then laminated onto the reagent layer 312. In dry analysis, a liquid sample is spotted on the spreading layer 313, passes through the spreading layer 313 and reaches the reagent layer 12 where a substance to be analyzed (i.e., analyte) is reacted with a reagent contained in the reagent layer 312. The optical density of the formed color is measured from the side of the support by reflection photometry to analyze the analyte in the liquid sample through the principle of colorimetry. The colorimetric analytical tape 31 may optionally contain other known layers such as light-reflecting layer, light-blocking layer, filtering layer, registration layer, water-absorbing layer, undercoating layer, etc. If desired, the spreading layer and the reagent layer may be combined to form a single layer.

The structure of the multilayer analytical element per se as shown in FIG. 5 is known. For example, the support 311 is a tape prepared from a material which is light-transmissive and water-impermeable. Examples of such material include polymers such as polyethylene terephthalate, polycarbonate of bisphenol A, polystyrene, cellulose ester (e.g., cellulose diacetate, cellulose triacetate, and cellulose acetate propionate) and the like. The thickness of the support 311 preferably is about 50 to about 300 μm, particularly 80 to 200 μm. The width of the support is preferably in the range of about 3 to 10 mm. The length of the support varies depending on the number of times of analysis expected per one roll, but is preferably so long that it has regions for analysis corresponding to the number of 100 to 600 tests, while there is no specific limitation with regard to the number of times of analysis.

The spreading layer 313 has a function capable of spreading a liquid sample over the said layer at a nearly constant rate per unit area in the horizontal direction without causing the unevenly distribution of components in said liquid, when said liquid is spotted on the surface of the spreading layer. The spreading layer 313 is formed from paper such as filter paper or knitted, woven or nonwoven fabric obtained from natural fiber or synthetic fiber or a mixture thereof. The spreading layer 313 may be one which is prepared from a porous material composed of fine polymer particles.

If desired, the spreading layer 313 may be impregnated with a hydrophilic polymer such as cellulose derivative, polyvinyl pyrrolidone, polyvinyl alcohol, polyacrylamide or the like or a surfactant such as a nonionic surfactant, a cationic surfactant, an anionic surfactant or an ampholytic surfactant to control the spreading of a liquid sample. The spreading layer may be impregnated with an appropriate buffer solution to conduct stable analysis.

The reagent layer 312 contains an appropriate reagent which is reacted with an analyte to thereby cause a change in color density which can be detected by colorimetry. Preferably, the reagent layer 312 is composed of one or more reagents dispersed in a hydrophilic colloid of gelatin, gelatin derivative, polyvinyl alcohol, polyacrylamide, polyvinyl pyrrolidone or the like which acts as a binder.

As another example of the analytical tape which can be used in the invention, there can be mentioned analytical tapes having ion-selective electrodes.

Another embodiment (B) of the present invention will be illustrated in more detail below by referring to the accompanying drawings.

Figure 6:
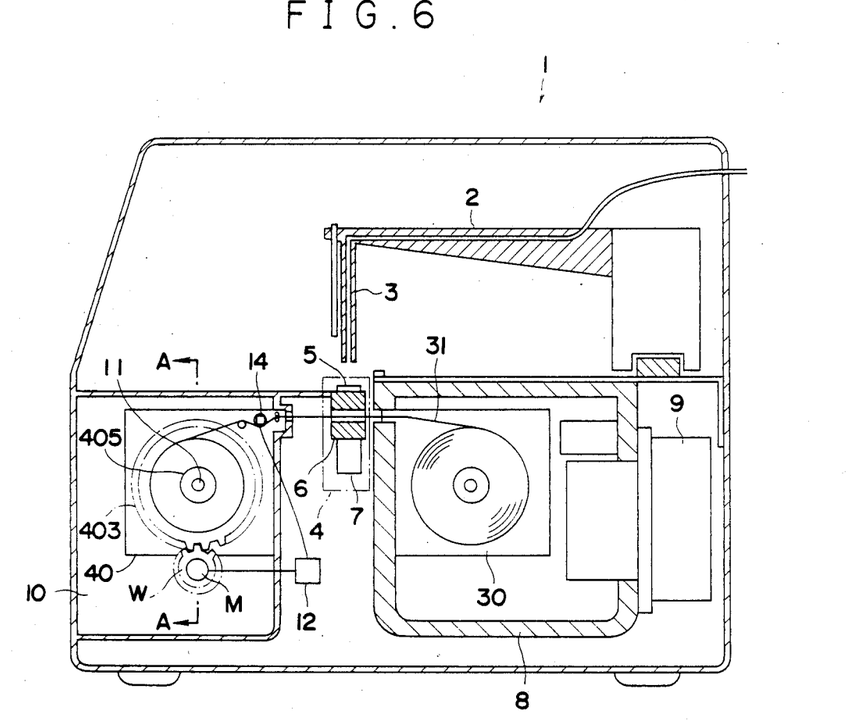
FIG. 6 is a schematic cross-sectional view of an embodiment of a biochemical analytical apparatus for use in colorimetric analysis, which is provided with a mechanism of another embodiment (B) according to the invention for supplying in sequence unused regions of an analytical tape by a predetermined length.

In FIG. 6, at the upper part of the biochemical analytical apparatus, 1 there is provided a means 2 for spotting a liquid sample containing analyte. A spotting nozzle 3 connected to the spotting means 2 is arranged just above an analytical section 4 which is arranged in the vicinity of the center of the analytical apparatus 1. The spotting means 2 is provided movably on the plane vertical to the direction of movement of the analytical tape. The analytical section 4 is provided with a shutter 5, an incubator 6 and a photometric measuring device 7. If desired, a plurality of the analytical sections may be placed on the line vertical to the direction of the movement of the analytical tape. Further, the analytical section 4 may be provided on the line in such a manner that the section can be moved in association with the spotting means 2. In the lower half part of the biochemical analytical apparatus 1, there is provided a low-temperature insulation container 8 having a cassette 30 for the unused portion of the analytical tape which is charged with an analytical tape 31. The insulation container 8 can be adjusted to have a desired low temperature and low humidity by a dehumidifying cooler 9 and can be kept at the adjusted low temperature and humidity. On the side opposed to the low-temperature insulation container 8, there is provided a wind-up chamber 10 which contains a cassette 40 for receiving the used portion of the analytical tape in such a way that the analytical section 4 is placed between the two cassettes.

In the wind-up chamber 10, a motor M for driving a reel 405 is provided. A control means 12 for controlling the start and stop of the motor M according to a signal from a light-receiving device 14.

Figure 7:
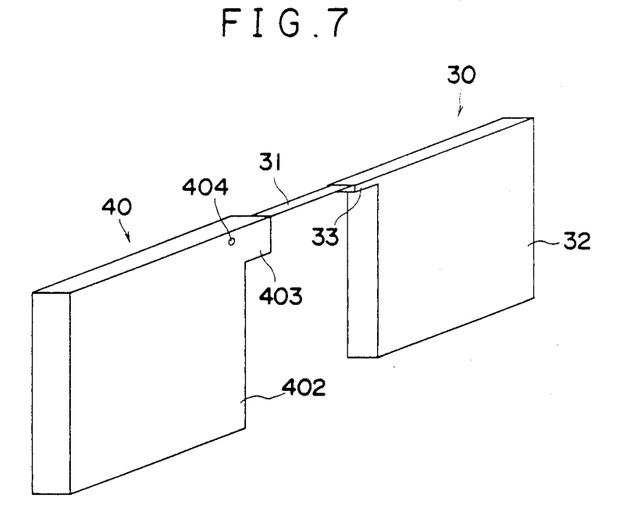
FIG. 7 is a perspective view of one embodiment of analytical tape cassettes to be used in the embodiment (B).

In FIG. 7, a cassette 30 for unused tape portion is a thick-wall rectangular case which has side plate 32 having a form of nearly a square, is slightly wider than the width of the analytical tape 31 and contains a roll of the analytical tape 31 therein. A port 33 for drawing out the analytical tape 31 is projecting from the case body. The cassette 40 for used tape portion is a case having similar form and size to those of the cassette 30 for unused tape portion. A port 403 for introducing the analytical tape 31 is projecting from the case body. A detecting window 404 is provided on the side plate 402 in the vicinity of the introducing port 403, and the used tape portion is introduced through said port 403 into the case and wound up.

Figure 8:
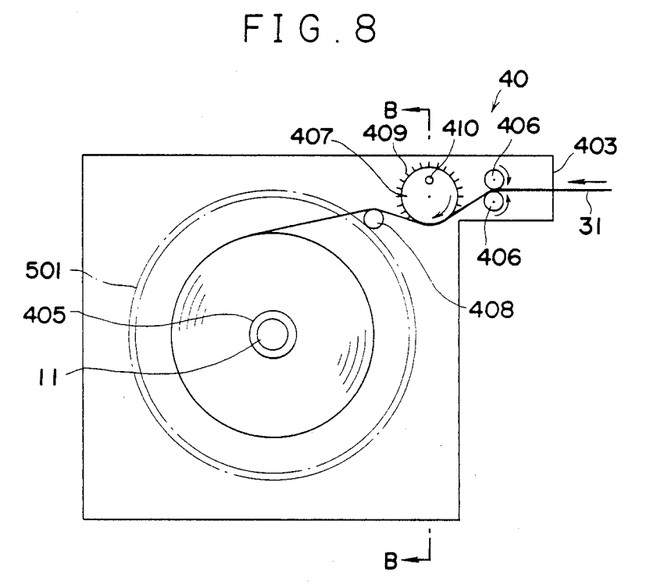
FIG. 8 is a cross-sectional view of a cassette for receiving the used portion of an analytical tape which shows one embodiment of an analytical tape cassette to be used in the embodiment (B) shown in FIG. 7.
Figure 9:
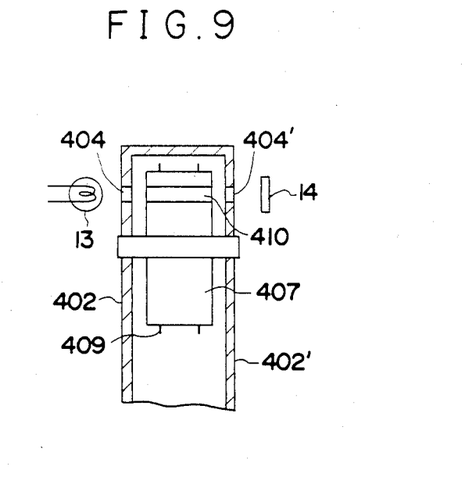
FIG. 9 is a partially enlarged cross-sectional view taken along the line B—B in FIG. 8.

In FIGS. 8 and 9, the analytical tape 31 is introduced through the introducing port 403 into the cassette 40 and wound around a reel 405. A spool wheel 501 is fixed to the reel 405, and teeth provided on the outer periphery of the spool wheel 501 are allowed to intermesh with the gear W of the motor M, whereby the reel 405 can be rotated by the rotation of the motor M.

Within the cassette part 40 in the vicinity of the introducing port 403, there are provided a pair of pinch rolls 406. A roller 407 and a guide roller 408 are rotatably provided at the back of the pinch rolls on the both sides 402, 402' of the cassette case. The pinch rolls 406, the roller 407 and the guide roller 408 are so arranged that the contact area of the roller 407 with the analytical tape 31 curved by the roller 407 is increased, when the analytical tape 31 is stretched between the pinch roll 406 and the guide roller 408. Many needle-like protrusions 409 are provided on the surface of the roller 407. Since the surface of the analytical tape 31 is generally composed of paper, knitted fabric, nonwoven or woven fabric or the like, the needle protrusions 409 can be locked with the surface of the analytical tape and the roller 407 follows the movement (traveling) of the analytical tape 31 and is accurately rotated without causing the slippage of the roller 407 on the analytical tape 31. The locking of the needle-like protrusions 409 with the analytical tape 31 can be easily made so that it is not necessary that the stretching between the pinch roller 406 and the guide roller 408 is tightly made.

The roller 407 is provided with a through-hole 410 on the plane vertical to the direction of the movement of the tape at an eccentric position on the flat side face of the roller 407. Detecting windows 404, 404' for detecting the hole 410 are provided on both sides 402, 402' of the cassette case at positions opposed to the hole 410 at the specific points of circle locus of the hole 410. In other words, when the hole 410 is positioned within an area formed by joining the detecting windows 404, 404' with each other during the rotation of the roller 407, light from a light-emitting device 13 such as light-emitting diode is passed through the hole and received by a light-receiving device 14 such as photo diode provided on the device 1 to thereby detect the hole 410.

The cassette for the analytical tape are constructed as described above. Accordingly, the number of times of the passage of the hole 410 can be detected through the detecting window 404 in terms of the rotation of the roller 407 which rotates in association with the movement of the analytical tape 31, whereby the feed length (i.e., supply length, or travelled length) of the analytical tape 31 can be detected. When the analytical tape 31 is moved in carrying out analysis with the biochemical analytical apparatus 1 as shown in FIG. 6 by using the above-described cassette, the feed length of the analytical tape 31 is detected in the manner as described hereinbefore. At the time when a predetermined length of the analytical tape 31 is moved, a signal is fed to the control means 12 and the rotation of the motor M is stopped by instructions from the control means 12 to thereby stop the rotation of the reel 405, thus stopping the movement of the analytical tape 31. At this moment, the unused tape portion is positioned in the analytical section 4 to carry out the analysis of a liquid sample. When the analysis is complete, a signal is fed to the control means 12, the motor M is started by instructions from the control means 12 to rotate the reel 405 and to move the analytical tape and the feed length is detected in the same manner as described above. At the time when a predetermined length of the analytical tape is supplied, the movement of the analytical tape 31 is stopped. By repeating the above operations, the analytical tape 31 can be fed intermittently to the analytical section accurately by a given length required for analysis.

The feed length of the analytical tape 31 can be arbitrarily changed by properly choosing the diameter of the roller 407, the number of revolutions thereof, etc.

The analytical tape in length required for one analytical operation may be supplied by one to several revolutions of the roller 407. Alternatively, the roller 407 may be provided with a plurality of holes (detectable marks) at regular intervals, and the analytical tape in length required for one analysis may be moved by less than one revolution (e.g., ½ revolution, ⅓ revolution, etc.) or a certain angle.

Many acute-angled protrusions may be provided on the surface of the roller 407 by forming a ratchet or rasp or by partially embedding solid particles in the surface of the roller 407, instead of providing the needle-like protrusions 409.

The roller 407 may be replaced with two rollers having a smooth circular surface, and analytical tape may be held between these two rollers by cooperation of these two rollers. In this case, the pinch rolls 406 may be replaced by guide roller or may be omitted.

The detecting window 404 may be in the form of a hole or the corresponding part to the window or the whole of the cassette case may be constructed from a transparent material.

Appropriate mark (e.g., color mark, magnetic layer, protrusion, etc.) may be provided at the same position as that of the hole 410 in place of the hole 410 and the number of angle of rotation of the roller 407 may be detected by detecting said mark optically (reflected light), electromagnetically or mechanically. It is not necessary that the detecting window 404 is in the form of a hole. Any form corresponding to the detectable mark can be used.

A rotor (preferably a rotating plate) synchronously rotated with the roller 407 may be provided inside or outside the cassette case and a detectable mark similar to that described above may be provided at an eccentric position on the flat side surface thereof. It is preferred to provide said rotor coaxially with the roller 407 outside the cassette case, because extra consideration for the cassette case is not required.

While an embodiment wherein the means for detecting the feed length of the analytical tape is provided within the cassette 40 has been illustrated above, said means can be provided within the cassette 30 for unused tape portion. In such a case, attention is to be paid that the analytical tape is not damaged by the pinch rolls 406 and the roller 407. For example, when the analytical tape 31 is held between two rollers, it is preferred that the edge parts thereof are held therebetween.

It can be determined according to the type of the analytical tape, analytical method, etc., whether the means for detecting the feed length of the analytical tape is provided within the cassette 40 or the cassette 30.

Figure 10:
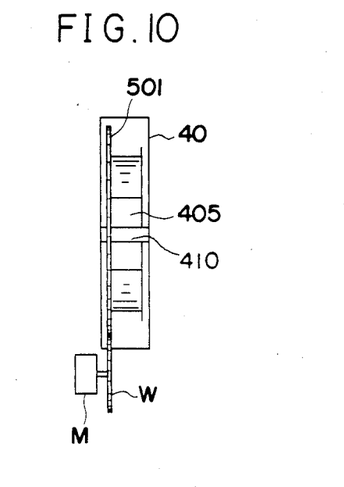
FIG. 10 is a cross-sectional view of a part of the cassette taken along the line A—A in FIG. 6.

While an embodiment wherein the reel 405 is rotated by the spool wheel 501 driven by the motor M is illustrated in FIG. 10, the hole 410 of the reel 405 may be locked with the wind-up shaft 11 and the wind-up shaft may be directly or indirectly rotated by the motor without providing the spool wheel 501.

If desired, the two cassettes 30, 40 may be prepared integrally.

The means for detecting the feed length of the analytical tape at a given length according to the present invention has a remarkable effect of controlling the feed length of the analytical tape so that the feed length of the analytical tape to be supplied at a given length required for analysis can be detected easily and accurately, and a predetermined length of the analytical tape can be accurately fed to the analytical section of the analytical apparatus.

We claim:

1. A mechanism for supplying in sequence unused regions of an analytical tape by a predetermined length to an analytical section arranged in an apparatus for biochemical analysis of a liquid sample wherein application of the liquid sample onto an unused region of the analytical tape, incubation of an applied sample, and photometric measurement of an incubated sample are performed at the analytical section, one end and the unused regions following said end of the analytical tape being encased in a cassette and another end of the analytical tape being encased in another cassette for receiving the used regions of the analytical tape after the photometric measurement is complete, which comprises:

driving means for moving an analytical tape to supply unused regions of the analytical tape to an analytical section;

detecting means for detecting a length of the unused regions of the analytical tape supplied to the analytical section comprising a roller which is arranged in contact with a surface of the analytical tape so that said roller rotates with movement of the analytical tape for the supply of the unused regions to the analytical section and a means for detecting one of a number of rotations and an angle of a rotation of said roller; and controlling means for controlling said driving means according to said one of said detected number of rotations and said angle of said rotation of said roller detected by said detecting means.

2. The mechanism as claimed in claim 1, wherein said detecting means for detecting said length of unused region is arranged between the analytical section and one of the cassette for unused regions of the tape and the cassette for the used regions of the tape.

3. The mechanism as claimed in claim 1, wherein said detecting means for detecting said length of the unused regions is arranged within one of the cassettes in the vicinity of one of an inlet and an outlet for the analytical tape.

4. The mechanism as claimed in claim 1, wherein said roller is provided with a plurality number of acute-angled protrusions on the outer periphery thereof.

5. The mechanism as claimed in claim 1, wherein an additional roller is provided at a position opposed to said roller and said analytical tape is held between these rollers.

6. The mechanism as claimed in claim 1, wherein said roller has a through-hole at an eccentric position on its side wall and said detecting means for detecting said one of said number and angle of the rotation of said roller comprises a combination of a light-emitting device and a light-receiving device for detecting light by allowing light to pass through said through-hole.

7. The mechanism as claimed in claim 1, wherein said roller has a detectable mark at an eccentric position on its side wall and said detecting means for detecting said one of said number and angle of the rotation of said roller comprises a means for detecting said mark.

8. The mechanism as claimed in claim 1, wherein said roller is provided with a rotor having a detectable mark at an eccentric position on its side face, said rotor rotating synchronously with said roller.

9. The mechanism as claimed in claim 1, wherein a flat guide plate is provided at a position opposed to said roller and said analytical tape is held between said roller and said guide plate.

* * * * *